(12) United States Patent
Junnarkar

(10) Patent No.: US 11,881,319 B2
(45) Date of Patent: Jan. 23, 2024

(54) TELEPHONE BASED TELE-HEALTH APPARATUS

(71) Applicant: Sachin S Junnarkar, Vernon Hills, IL (US)

(72) Inventor: Sachin S Junnarkar, Vernon Hills, IL (US)

(*) Notice: Subject to any disclaimer, the term of this patent is extended or adjusted under 35 U.S.C. 154(b) by 407 days.

(21) Appl. No.: 17/248,027

(22) Filed: Jan. 6, 2021

(65) Prior Publication Data
US 2022/0068505 A1 Mar. 3, 2022

Related U.S. Application Data (60) Provisional application No. 63/118,751, filed on Nov. 27, 2020, provisional application No. 63/072,961, filed on Sep. 1, 2020.

(51) Int. Cl.
*G16H 80/00* (2018.01)
*G16H 30/20* (2018.01)
(Continued)

(52) U.S. Cl.
CPC ............ *G16H 80/00* (2018.01); *A61B 1/227* (2013.01); *A61B 5/0022* (2013.01);
(Continued)

(58) Field of Classification Search
CPC ........ G16H 80/00; G16H 40/67; G16H 30/20; G16H 50/30; G16H 30/40; A61B 7/02;
(Continued)

(56) References Cited

U.S. PATENT DOCUMENTS 5,989,186 A * 11/1999 Alatriste ............ A61B 1/00105
600/528
8,325,245 B2 * 12/2012 Leard ..................... H04N 23/60
348/222.1
(Continued)

FOREIGN PATENT DOCUMENTS

GB 2534019 A * 7/2016 ............. A61B 1/227

OTHER PUBLICATIONS

International Search Report and Written Opinion issued by the International Searching Authority for Application No. PCT/US2021/047833, dated Dec. 6, 2021, 10 pages.
(Continued)

*Primary Examiner* — Jeremy A Luks
(74) *Attorney, Agent, or Firm* — IPHORIZONS PLLC; Narendra Reddy Thappeta (57) ABSTRACT

A tele-health apparatus includes a telephone having a microphone, an auscultation piece to acquire sounds, and a solid medium acoustically coupling the auscultation piece to the microphone. The auscultation piece is part of a stethoscope, and the solid medium is a windpipe of the stethoscope. The tele-health apparatus also includes an otoscope operable to be disposed in front of a camera of the telephone. A clip holds the stethoscope and the otoscope, and is fixed to the phone. Software modules installed in the telephone enable the tele-health apparatus to engage a user in a two-way audio and/or video consultation with a physician at a remote device in real-time.

8 Claims, 6 Drawing Sheets

(51) Int. Cl.

| | |
|---|---|
| *G16H 30/40* | (2018.01) |
| *G16H 50/30* | (2018.01) |
| *A61B 5/021* | (2006.01) |
| *A61B 5/1455* | (2006.01) |
| *A61B 5/00* | (2006.01) |
| *A61B 5/026* | (2006.01) |
| *A61B 5/0295* | (2006.01) |
| *A61B 1/227* | (2006.01) |
| *A61B 7/02* | (2006.01) |
| *A61B 5/0205* | (2006.01) |
| *H04M 1/02* | (2006.01) |
| *H04M 1/215* | (2006.01) |
| *H04N 7/18* | (2006.01) |
| *G16H 40/67* | (2018.01) |
| *A61B 5/024* | (2006.01) |

(52) U.S. Cl.
CPC .......... *A61B 5/0205* (2013.01); *A61B 5/0261* (2013.01); *A61B 5/0295* (2013.01); *A61B 5/02116* (2013.01); *A61B 5/14552* (2013.01); *A61B 5/6898* (2013.01); *A61B 5/7253* (2013.01); *A61B 5/7278* (2013.01); *A61B 5/7465* (2013.01); *A61B 5/7485* (2013.01); *A61B 7/02* (2013.01); *G16H 30/20* (2018.01); *G16H 30/40* (2018.01); *G16H 40/67* (2018.01); *G16H 50/30* (2018.01); *H04M 1/0264* (2013.01); *H04M 1/2155* (2013.01); *H04N 7/185* (2013.01); *A61B 5/0077* (2013.01); *A61B 5/02433* (2013.01); *A61B 2576/00* (2013.01)

(58) Field of Classification Search
CPC ..... A61B 1/227; A61B 5/0022; A61B 5/0205; A61B 5/02116; A61B 5/0261; A61B 5/0295; A61B 5/14552; A61B 5/6898; A61B 5/7253; A61B 5/7278; A61B 5/7465; A61B 5/7485; A61B 5/0077; A61B 5/02433; A61B 2576/00; H04N 7/185; H04M 1/0264; H04M 1/2155
See application file for complete search history.

(56) References Cited

U.S. PATENT DOCUMENTS

| | | | |
|---|---|---|---|
| 10,349,893 B2 | 7/2019 | Lee et al. | |
| 11,172,825 B1* | 11/2021 | Ayanruoh | A61B 3/12 |
| 2014/0275817 A1* | 9/2014 | Script | A61B 5/1135 |
| | | | 600/324 |
| 2015/0087926 A1 | 3/2015 | Raz et al. | |
| 2015/0104027 A1 | 4/2015 | Mulumudi et al. | |
| 2015/0250381 A1 | 9/2015 | Bedard et al. | |
| 2016/0302666 A1 | 10/2016 | Shaya | |
| 2017/0296138 A1 | 10/2017 | Shams et al. | |
| 2017/0303857 A1* | 10/2017 | Perkins | A61B 1/233 |
| 2018/0192965 A1 | 7/2018 | Rose et al. | |
| 2020/0029837 A1 | 1/2020 | Joudi | |
| 2020/0121189 A1 | 4/2020 | Farr | |
| 2021/0068646 A1* | 3/2021 | Zhang | A61B 5/7267 |

OTHER PUBLICATIONS

TytoHome General Operation User Guide, https://mtelehealth.com/wp-content/uploads/2019/06/Document-760-00066-B01-TytoHome-General-Operation-User-Guide-for-Consumer-v3.2-2018-12-01.pdf, Document Version 3.2, Document No. 760-00066 B01, Dec. 2018, 67 pages.

TytoHome Tyto Stethoscope User Guide, https://mtelehealth.com/wp-content/uploads/2019/06/Document-760-00051-B01-TytoHome-Tyto-Stethoscope-User-Guide-v3.2-2018-12-01.pdf, Document Version 3.2, Document No. 760-00051 B01, Dec. 2018, 15 pages.

TytoHome Tyto Otoscope User Guide, https://static-cloud.tytocare.com/4_2/manuals/en-us/760-00048_C01_TytoHome-Tyto%20Otoscope.pdf, Document No. 760-00048 C01, Aug. 2019, 18 pages.

Tyto Care Joins Epic App Orchard to Offer One-of-a-kind Integrated Telehealth Service to Patients and Health Providers, https://www.tytocare.com/professionals/epic-app-orchard/, May 22, 2019, 03 pages.

On-demand medical exams for your patients, https://www.tytocare.com/professionals/products/tytohome/, downloaded circa Sep. 18, 2020, 02 pages.

How Tyto Works, https://www.tytocare.com/how-tyto-works/, Feb. 22, 2020, 05 pages.

Steth IO is a Stethoscope in a Smartphone • Medtech Impact On Wellness, https://www.medtechimpact.com/steth-io-functions-like-stethoscope-yet-contained-in-smartphone/#:~:text=Steth%20IO,%20is%20built%20directly,up%20to%20a%20patient's%20chest., downloaded circa Sep. 18, 2020, 06 pages.

Steth IO telehealth, https://stethio.com/telehealth/, Aug. 15, 2020, 10 pages.

Steth IO—Clinicains, https://stethio.com/clinicians/, Aug. 15, 2020, 04 pages.

Coala Heart Monitor, https://www.coalalife.com/se/english/, Oct. 31, 2020, 11 pages.

EKO—DUO ECG+ Digital Stethoscope, https://shop.ekohealth.com/products/duo-ecg-digital-stethoscope, Apr. 2, 2020, 16 pages.

TYM Smartphone Otoscope, https://www.foursquare-healthcare.co.uk/tym-smartphone-otoscope/, Aug. 9, 2020, 06 pages.

StethoMe, https://stethome.com/, Oct. 28, 2020, 05 pages.

* cited by examiner

TELEPHONE BASED TELE-HEALTH APPARATUS

PRIORITY CLAIM

The instant patent application is related to and claims priority from the following two provisional US patent applications:
- A) Entitled, "Synchronous Tele-Health Diagnostic System Integrated With Smart Devices", Ser. No. 63/072,961, Filed: 1 Sep. 2020, and
- B) Entitled, "Synchronous Tele-Health Diagnostic System Integrated With Smart Devices", Ser. No. 63/118,751, Filed: 27 Nov. 2020, both of which are incorporated in their entirety herewith to the extent not inconsistent with the description herein.

BACKGROUND

Technical Field

Embodiments of the present disclosure relate generally to healthcare apparatuses, and more specifically to a telephone-based tele-health apparatus.

Related Art

Tele-health apparatuses enable doctors and other medical personnel to remotely serve persons requiring medical assistance. Telephones refer to devices which enable two or more persons to conduct voice and/or video calls. While telephones were wire-based in early evolution of the technology (referred to as Plain Old Telephone Systems, POTS), telephones are now available in the form of mobile/smart phones which communicate wirelessly on 5G/4G/3G, WiFi etc., communication standards.

Because of the ubiquity of telephones, there is a constant demand to provide tele-health apparatuses which leverage the capabilities of telephones.

BRIEF DESCRIPTION OF THE VIEWS OF DRAWINGS

Example embodiments of the present disclosure will be described with reference to the accompanying drawings briefly described below.

FIG. 6A is an exploded diagram illustrating the parts of an otoscope in a telephone-based tele-health apparatus in an alternative embodiment of the present disclosure.

FIGS. 6B and 6C respectively show two different views of an otoscope in assembled form, in the alternative embodiment.

FIG. 7 is a diagram illustrating a fiber-holder ring used in an otoscope in a telephone-based tele-health apparatus in an alternative embodiment of the present disclosure.

FIG. 8 is a block diagram of several application modules executed in a telephone-based tele-health apparatus, in an embodiment of the present disclosure.

FIGS. 9A through 9L are illustrations of example screens displayed on a telephone-based tele-health apparatus enabling interaction of a user with features provided by the apparatus.

FIG. 10 is a block diagram of a telephone implemented according to several aspects of the present disclosure.

In the drawings, like reference numbers generally indicate identical, functionally similar, and/or structurally similar elements. The drawing in which an element first appears is indicated by the leftmost digit(s) in the corresponding reference number.

DETAILED DESCRIPTION

1. Overview

According to an aspect of the present disclosure, a stethoscope and an otoscope are fitted to a telephone. The telephone may, for example, be a readily available, off-the-shelf device such as a mobile phone. The stethoscope is connected to the microphone port of the telephone, and the otoscope is fitted to the telephone such that it couples light to a camera in the telephone. The stethoscope may be a passive mechanical and acoustic attachment (to the telephone), and the otoscope may be a passive mechanical and optical attachment (to the telephone). The term 'passive' with respect to a part implies that there are no components in that part that require electric power for its operation in accordance with features described herein.

In conjunction with corresponding application modules executable in the telephone, the integrated tele-health apparatus (telephone plus stethoscope plus otoscope plus application modules) enables a two-way audio and/or video consultation between a user and a remote medical professional or physician. Synchronous, real-time diagnostic data obtained by the apparatus via the stethoscope and otoscope (operated by the user as directed by the remote physician) are made available to the physician, who can then prescribe the required treatment and medicines. Thus, the tele-health apparatus can provide a tele-health solution that may be equivalent to primary care physician in-office examination.

Several aspects of the present disclosure are described below with reference to examples for illustration. However, one skilled in the relevant art will recognize that the disclosure can be practiced without one or more of the specific details or with other methods, components, materials and so forth. In other instances, well-known structures, materials, or operations are not shown in detail to avoid obscuring the features of the disclosure. Furthermore, the features/aspects described can be practiced in various combinations, though only some of the combinations are described herein for conciseness.

2. Telephone-Based Tele-Health Apparatus

Figure 1:
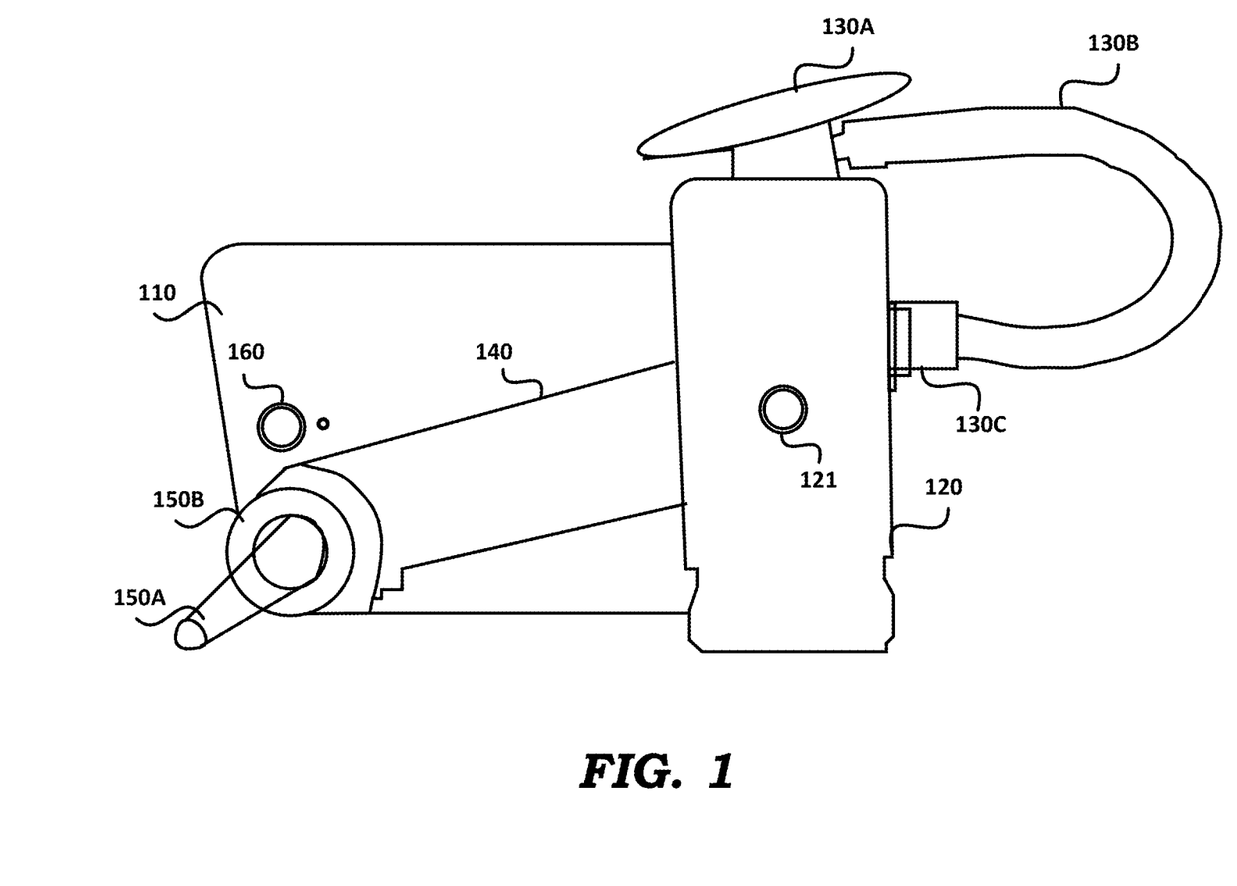
FIGS. 1 through 4, 5A and 5B are diagrams of different views of a telephone-based tele-health apparatus in an embodiment of the present disclosure.
Figure 2:
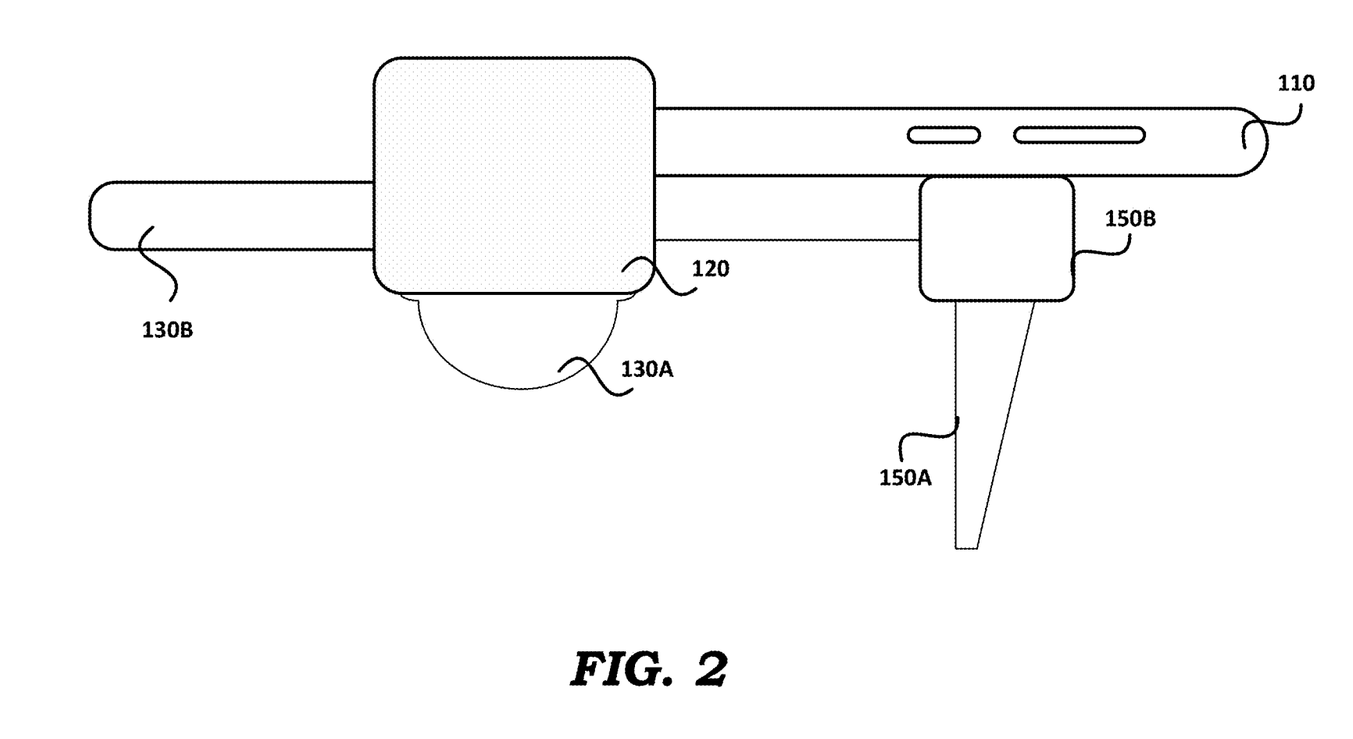

FIGS. 1 through 4, 5A and 5B are diagrams of different views of a telephone-based tele-health apparatus (Apparatus 100) in an embodiment of the present disclosure. In the embodiment, a smart phone (110) is used as the telephone. As is well-known in the relevant arts, a smart phone is a mobile device that combines cellular and computing capabilities into one unit. A smart phone typically contains a mobile operating system, which enables applications to be loaded on the smart phone, thereby enabling features such as for example, web browsing, audio and video players, cameras, etc., in addition to traditional phone functions such as voice calls. However, in other embodiments, other devices (which permit voice calls) such as tablet PC (personal computer), iPads, internet-connected chrome books, computers, IoT (Internet of Things) enabled devices as well as wired telephones, IP (internet protocol) phones can be used instead. FIG. 1 is shown containing smart phone 110, clip 120, stethoscope 130, otoscope X-Y adjuster 140 and otoscope 150.

Figure 5A:
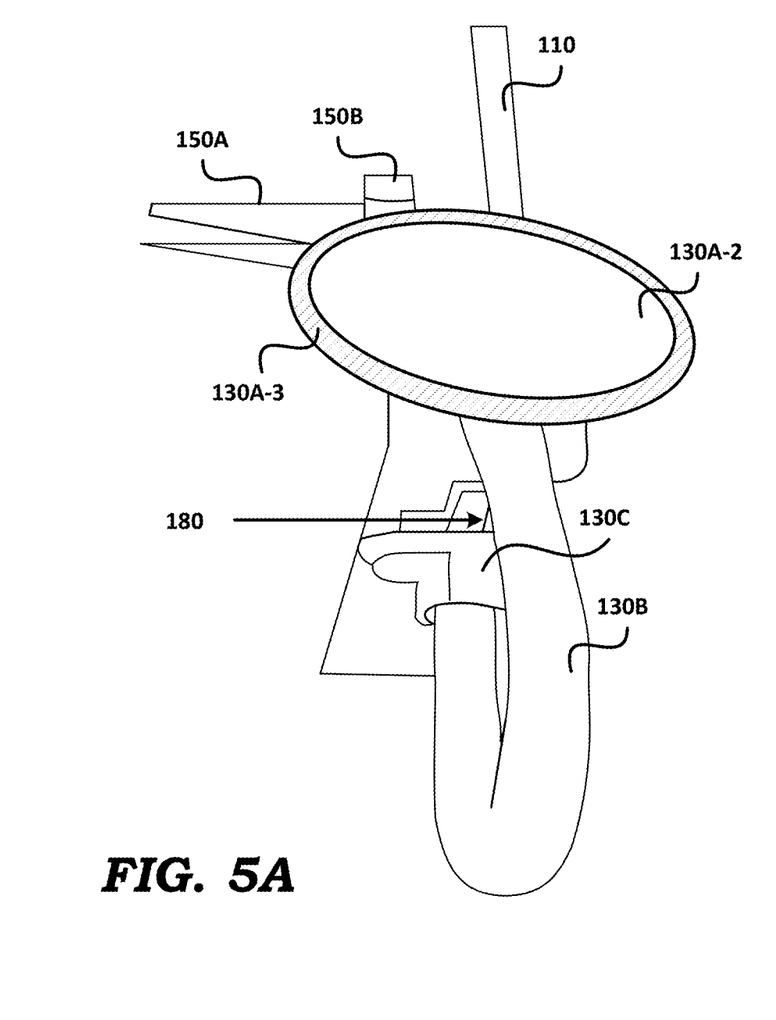
Figure 5B:
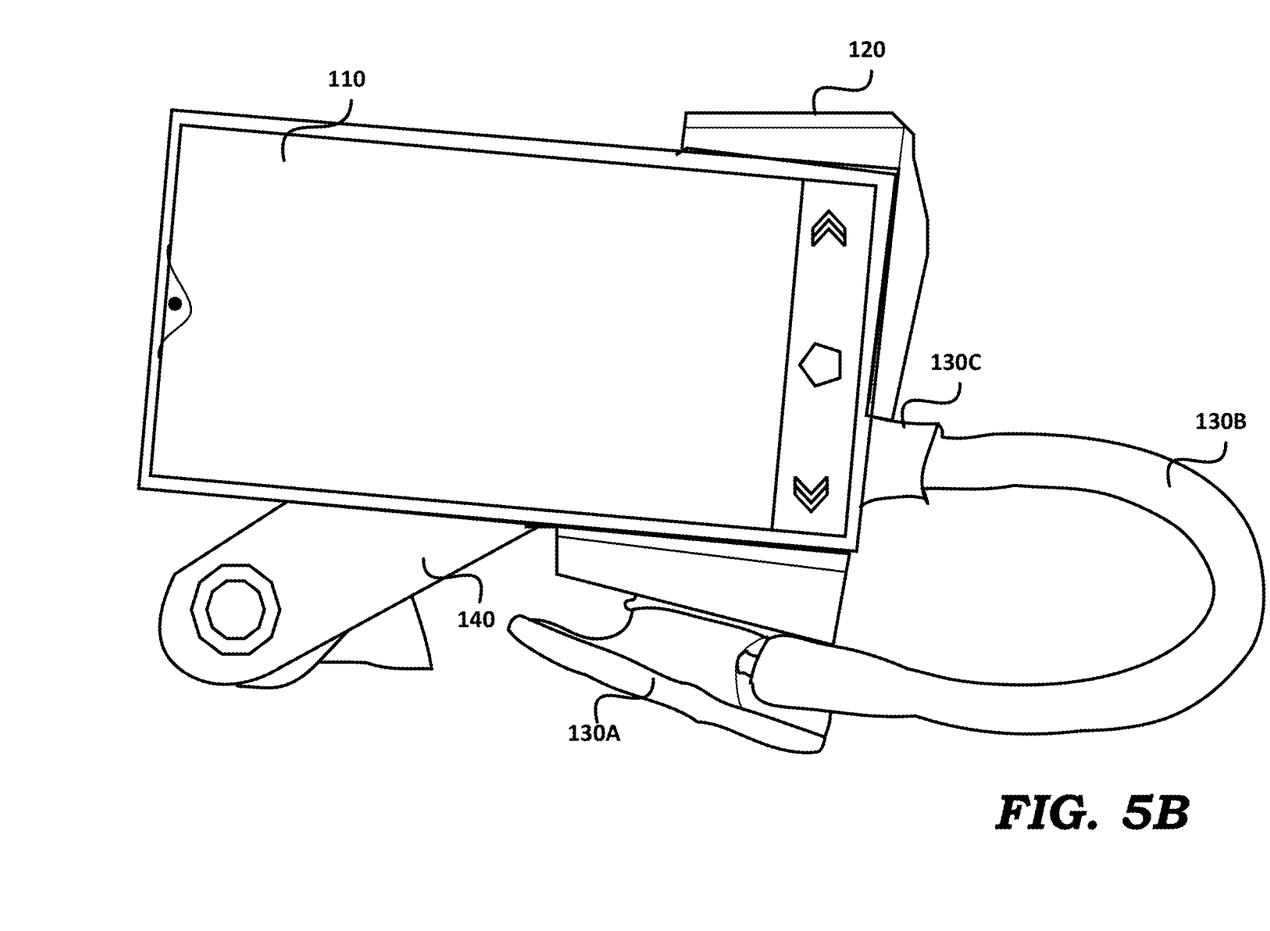

Smart phone 110 represents an off-the shelf mobile telephone with an operating system, and supports addition (installation) of application modules, and supports circuit-switched and/or packet-switched voice and/or video calling. Smart phone 110 is equipped with one or more microphones, as well as one or more cameras. A microphone port 180 of a microphone is shown in FIG. 5A. Thus, a voice signal received at microphone port 180 is converted into an electronic signal suitable for transmission to the other end, where another phone or a device such as a computer, tablet or otherwise reproduces the voice signal from the electronic signal. A camera port 160 of a camera on the back-side of smart phone 110 is shown in FIG. 1. Camera port 160 is used in conjunction with the otoscope, as described below. Phone 110 also has a front-side camera, which is used during a video call, thus enabling the remote physician to "see" the patient/user.

Clip 120 is a mechanical assembly or harness and is designed to grip the outer edges and back of smart phone 110 using, for example, spring action or a tightening screw. Clip 120 is more clearly shown in FIGS. 1 and 3. Stethoscope 130 and otoscope 150 are attached (as noted below) to clip 120, and thereby are secured to smart phone 110. Clip 120 is sized such that it does not interfere with device controls on smart phone 110. Clip 120 may also be designed so as to meet the device (smart phone 110) manufacturer's attachment criteria, if any.

Figure 4:
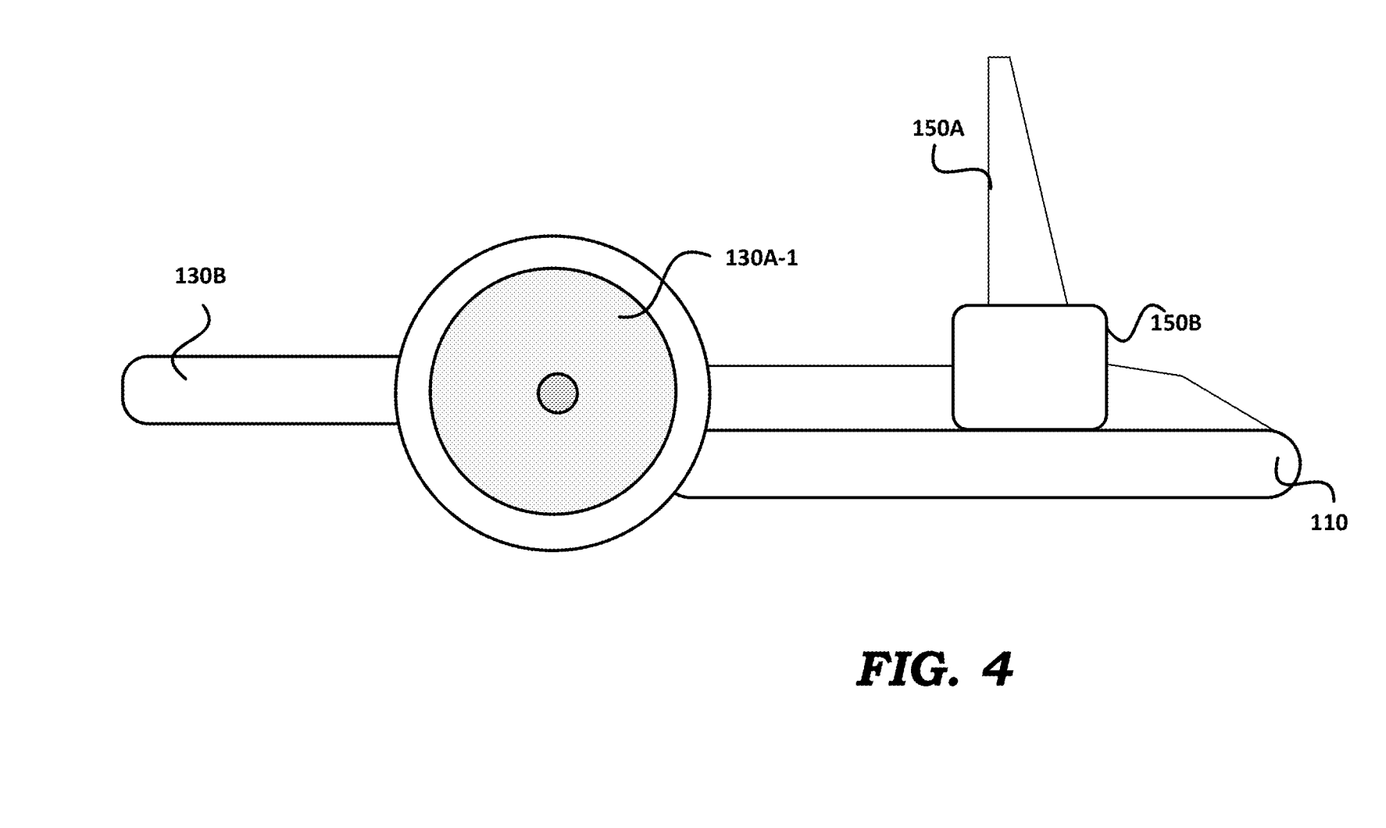

Stethoscope 130 is made up of auscultation piece (or chest piece) 130A, wind pipe 130B and coupling piece 130C. Auscultation piece 130A is in turn made of a flexible diaphragm, an acoustic chamber and a ring or nut to elastically fasten the flexible/elastic diaphragm to the acoustic chamber. FIG. 4 shows the acoustic chamber 130A-1 more clearly. FIG. 5 shows flexible diaphragm 130A-2 and ring or nut 130A-3 more clearly. Acoustic chamber 130A-1 may be made, for example, of metal or rigid hard non-porous plastic. Auscultation piece 130 is used for acquiring sounds, such as for example, heart and lung sounds, or in general, sounds inside a patient's body. Auscultation piece 130 may need to be placed close to the source of the sound.

Wind pipe 130B carries acoustic waves from the auscultation piece 130A to the microphone port/opening of smart phone 100, and may be a hollow rubber tube, for example (solid medium, in general). One end of the wind pipe 130B is connected to the auscultation piece 130A, while the other end is connected to coupling piece 130C. Coupling piece 130C couples auscultation audio waves to smart phone 110's microphone outlet/port while securing the wind pipe through a compression fit. For cushioning and optimal air coupling into the microphone hole/holes one or more suction cups or soft rubber couplers is/are used. This coupling allows for user voice to be captured without significant attenuation and the user can continue regular audio (via the microphone) and/or video/visual communication without interruption or significant degradation.

Auscultation piece 130 is secured to clip 120 (when not in use) by double-sided tape or glue or a hook. Alternatively, auscultation piece 130 can be secured to clip 120 using a screw, hook, temporary stowing mechanism or be permanently molded as part of clip 120, in which case the chest piece can't be removed but provides an advantage of compactness. Sounds received via stethoscope 130 and the microphone port of smart phone 110 are processed and/or transmitted (in real-time, for example) by application modules in smart phone 110 to a remote device (such as, for example, another phone) for analysis by a doctor (physician). The application modules can also simultaneously play the sounds on a local speaker/earphones of smart phone 110, or record them locally in smart phone 110. It is noted here that, since microphone of phone 110 is employed for receiving heart auscultations, an ear phone without a microphone (or microphone disabled) needs to be used by the user. Alternatively, the tele-health application can be designed to force the software that controls the (earphone+external microphone) headset to use the phone's microphone port 180 and not the external microphone provided with the headset.

Although windpipe 130B in the Figures is shown to be rather short, the length of windpipe 130B can be much longer in practice. In an embodiment, the length of windpipe 130B is at the maximum 300 centimetres with no minimum length limit. Due to such length, the user can simultaneously view the physician on display of phone 110, listen and converse with the physician, allow the physician to see the user via the front-side camera of phone 110, as well as simultaneously operate stethoscope 130 to capture heart and lung auscultation audio. Such a facility enables easy use by the user especially if the user is elderly, differently-abled person, or a sick patient, since the user now does not need to juggle with two or more devices simultaneously causing asynchronous and confusing data streams for the physician as well as the patient, and thereby deteriorating the diagnostic quality. Also, user anxiety associated with losing contact with the remote physician is absent in this embodiment. However, in an alternative embodiment, the windpipe 130B is eliminated and chest piece 130A is directly coupled to coupling piece 130C.

Figure 3:
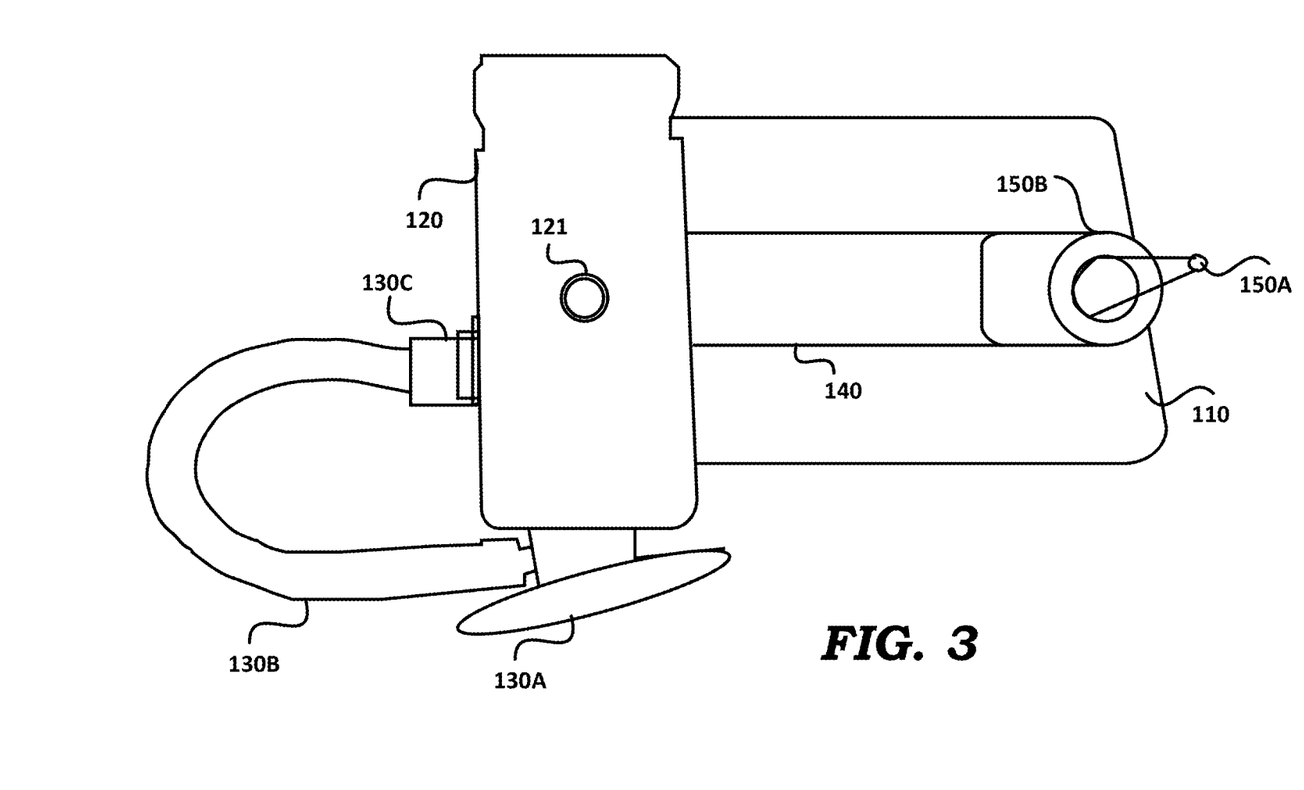

Otoscope 150 is made up of speculum 150A and lens holder 150B. Speculum 150A and lens holder 150 are attached to otoscope X-Y adjuster 140, which in turn is pivoted via pivot mechanism 121 on clip 120. Lens holder 150B houses a magnifying lens, and the focal length of the lens is adjustable by a screw to enable light from the viewed source to be focused onto camera port 160. Otoscope 150 can be swiveled via the pivot mechanism 121, using radial co-ordinates to be positioned in front of camera port 160. An alternative embodiment of the pivot mechanism 121 employs a Cartesian X-Y translation frame. FIG. 3 shows otoscope 150 positioned in front of the camera port. Otoscope 150 enables a user/patient of smart phone 110 to obtain videos or still pictures of, for example, ear, nose and throat, etc., of a user/patient, by positioning speculum 150A in the part to be viewed. Videos and still pictures (i.e., images) obtained using otoscope 150 and camera port 160 are processed and/or transmitted (in real-time, for example) by application modules in smart phone 110 to a remote device (such as, for example, another phone, computer or a smart communication device) for analysis by a physician. The application modules can also simultaneously render the videos and/or still pictures on a display screen of smart phone 110, or record them locally in smart phone 110.

In an alternative embodiment of the present disclosure, the otoscope functionality is augmented to also use the flash LED (light emitting diode) of smart phone 110 in conjunction with a light guide to illuminate the object desired to be viewed and analyzed. FIG. 6A is a diagram showing an exploded view of the otoscope in the alternative embodiment. When in use, otoscope 600 shown there is positioned such that light collected by the otoscope impinges on a camera port of smart phone 110, such as camera port 160 (FIG. 1). Similar to otoscope 130, otoscope 600 may also be fitted to swivel on a clip such as clip 120 as illustrated in FIGS. 1-4, 5A and 5B. Alternatively, otoscope 600 may be attached to smart phone 110 using double-sided sticky tape (removable) or elastic band mechanisms.

Referring to FIG. 6A, otoscope 600 shown there is made of parts speculum 610, optic fiber holder ring 620, lens 630, tunnel 640 and cylinder 660. Speculum 610 functions similar to speculum 150A of FIG. 1 to collect light from a viewed object (ear, nose, etc.). In addition, speculum 160 has fiber guide paths on it through which optic fibers can channel light from a light source such as the flash LED of smart phone 110 onto the object to be viewed. Example guide paths 615, which would be in the speculum, are shown in FIG. 6A.

Fiber holder ring 620 contains holes through which individual optic fibers are passed and thus secured in place when the components of FIG. 6A are assembled. The holes are aligned with the guide paths in speculum 610. The number of fibers, fiber diameter and therefore the holes in ring 620 may be determined based on the size of the flash LED. Fiber holder ring 620 is shown separately and in greater detail in FIG. 7, in which only one hole 711 is marked. The entire fiber bundle made of individual fibers (such as 710) are collected (bundled together, as indicated by marker 720) and optically coupled to the flash LED through compression, by which the geometric plane containing the bundled fibers' faces (720 of FIG. 7, for example) coincides with the geometric plane that contains the LED flash outer surface without any air gap, and the center of the fiber bundle approximately coincides with the center of the flash to allow for optimum coupling of the light emanating from the flash to enter the bundled fibers.

Cylinder 660 attaches to ring 620 at one end, and the other end is attached to an X-Y adjuster (not shown) such as adjuster 140 of FIG. 1. Alternatively, the X-Y adjuster is not used, and cylinder 660 is directly attached to camera port using suitable mechanisms (such as for example double-sided sticky tape), such that the camera port is right below the bottom part (690) of cylinder 660. Lens 630 is used for magnification, and is fitted to be within cylinder 660 and concentric to it.

Tunnel 640 receives the fiber bundle from ring 620, and routes the bundle to the flash LED of the camera (indicated in FIG. 7 by marker 720. Tunnel 640 may be designed using flexible optical fiber/fibers or light pipes. The flash lens (not shown) of the camera on smart phone 110 would be at the bottom of tunnel 640. Slot 650 is an adjustment mechanism to adjust the center of the light-carrying fiber bundle to coincide with that of the flash, while achieving one-to-one light coupling between the flash and fibers. This mechanism allows for adjusting for flash location differences in different smartphones. The entire otoscope assembly can be pivoted around the pivot point (similar to pivot point 121 of FIG. 1) or be mounted on a Cartesian X-Y stage to allow the user to approximately align the back-side camera center with lens tower center (i.e., cylinder 660). Tab 640A and 640B (FIG. 6C) can be pulled in and out of the assembly so as to allow for flash-fiber center alignment. The light carrying fiber bundle (e.g., 720 shown in FIG. 7) is tied and routed through a hole inside tab 640B to allow for alignment of the plane of the fiber bundle with that of the flash lens.

FIGS. 6B and 6C depict two different views of otoscope 600 in assembled form.

It is noted here that the otoscope (150 or 600) contains optical attachment filters (attached to the otoscope/optical attachment) to convert IR to visible wavelength. Thus, in FIG. 1, the filter would be contained in the lens holder 150B along with the lens. Similarly, in FIG. 6A, the filter would be contained in cylinder 660 proximal to lens 630. The reason for the addition of the filters is that a smart phone camera such as that of phone 110 may not detect IR (infra-red light), and IR from the human body has rich information. The optic filters convert IR into useful visible light spectrum. Ambient visible light is blocked using black colored soft rubber blockers coupled to bottom surface 690, so as to prevent ambient light from getting into the otoscope, as well as to avoid making scratches on the smartphone camera lens, body and flash.

It may be appreciated that apparatus 100 being a single apparatus (single piece), may lend to easy use by a patient. It is noted here that most of the existing devices or systems available for point-of-care diagnostics appear to require additional hardware to be implemented within the device, and suffer from redundant communication infrastructure and/or asynchronous streams of the two devices making diagnosis confusing and inaccurate. Alternatively, the prior systems appear to require a dedicated, redundant communication infrastructure in order to function and provide point-of-care diagnostics. Such requirements represent usability problems where the caregiver or a patient needs at least two different devices in order to get the point-of-care diagnostics information relayed to physician or a health care provider, albeit asynchronously. Using two devices is problematic in the case where patient is either non-cooperative or constrained and causes diagnostic inaccuracies. For example, if a parent or a caregiver for a senior, differently abled person, or a sick patient makes a tele-health call to a physician, from a usability perspective, they have to juggle with two devices simultaneously causing asynchronous and confusing data streams for the physician as well as the patient, there by deteriorating the diagnostic quality. In cases where there is no point of care diagnostic equipment available, the physician has to do a diagnosis and prescribe medication based solely on video stream and or patient interview. These disadvantages make current devices or systems very ineffective to provide quality health care to the patient.

Apparatus 100 on the other hand enables a user to view as well as speak with the physician at the remote device even while handling stethoscope 130. Also, when using the otoscope, phone 110 maintains audio as well as video contact (video contact via front-side camera) with the physician intact by automatically starting the speaker of the phone when the user is using the otoscope (for example for examination of the ear), as opposed to having the audio channeled through the headphones which the user may find difficult to use simultaneously with the otoscope.

Smart phone 110 contains (or can be loaded with) application modules that integrate and synchronously (in real-time) transmit diagnostic information obtained via stethoscope 130 and otoscope 150/600 to a remote device. Smart phone 110 also contains application modules for determining pulse rate, temperature, blood pressure and pulse oxygen content of the user from images/videos obtained from a finger-press on camera port 160. In combination with corresponding software on a remote device/terminal, apparatus 100 provides a two-way audio and/or video consulting capability for remote diagnosis, archival, medicine prescription (or treatment advice) and billing. The operation of some the application modules in smart phone 110 is described next.

3. Application Modules

FIG. 8 is a block diagram of several application blocks/modules that can execute in smart phone 110. The specific blocks are shown merely by way of illustration, and there can be many more application blocks that can execute in smart phone 110. Further, the operations of some of the blocks can be combined in a single block also. The term "software module" as used herein can refer to a single block or a combination of multiple blocks. Further still, a mobile operating system (OS) may be present in phone 110.

It is noted here that one or more of the blocks of FIG. 8 may rely on other application modules (not shown, but contained in the tele-health application—which refers to the combination of all the modules as a whole) for decision making, forwarding data to a next module etc. Accordingly, it is assumed in the following description that the tele-health application contains an application module control block (AMCB) that generates control signals for the blocks of FIG. 8 (where needed). One or more of such control signals may be generated based on the user's interaction or inputs to the tele-health application. As an example, when a user presses button 941 in the screen shown in FIG. 9H, the tele-health application 'knows' that the user is going to obtain heart auscultation audio. Therefore, the AMCB sends a signal to microphone interface block 805 to forward the audio data received on path 801 to heart auscultation audio block 810, and not to lung auscultation audio block 815.

In an embodiment, one or more of the blocks of FIG. 8 may be designed according to WebRTC (Web Real-Time Communication) technology to enable real-time or synchronous exchange of various diagnostic and other information between phone 110 and a remote device. As is well known in the relevant arts, WebRTC refers to a free, open-source project that provides web browsers and mobile applications with real-time communication (RTC) via simple application programming interfaces (APIs). Thus, for example, microphone interface block 805 and camera interface block 830 may be implemented using getUserMedia API (provided by WebRTC), and transmit block 890 may be implemented using RTCPeerConnection API (also provided by WebRTC).

Referring now to FIG. 8, microphone interface block 805, heart auscultation audio block 810, lung auscultation audio block 815 and audio play block 820 operate on digitized audio data. Microphone interface block 805 receives digitized audio data from microphone port of phone 110, and via audio hardware (which includes Analog-to-Digital Converter (ADC)) of phone 110 when stethoscope 130 is used to obtain audio information. Microphone interface block 805 may be implemented using application programmers interface (API) function call provided by the operating system in phone 110. Microphone interface block 805 forwards the received audio data to the corresponding one of blocks 810 and 820, depending on whether the audio data represents heart auscultation audio or lung auscultation audio. Microphone interface block may make such determination based on inputs from the application module control block (AMCB) as noted above. Referring to FIG. 1, heart or lung auscultation audio is obtained by the user placing auscultation piece 130A to either the chest or lung area of the user. The user may be guided via phone 110 by a physician at the remote end to place auscultation piece 130A appropriately.

Heart auscultation audio block 810 applies digital filtering to remove noise from the received heart audio data to obtain filtered heart audio data. Based on inputs from the application module control block note above, heart auscultation audio block 810 may forward the filtered data to one or more of audio play block 820, storage block 880 and transmit block 890. The inputs from the application module control block may be based on whether real-time local play, remote play, local storage, remote or cloud storage, archival and retroactive play are required to be performed—these could again come from user inputs to the tele-health application. In an embodiment of the present disclosure, heart audio auscultation data are simultaneously (synchronously) played locally in phone 110 as well as in a remote device (after concurrent or delayed transmission as required by the physician at the remote device), enabling real-time and/or asynchronous diagnosis by the physician at the remote device.

Lung auscultation audio block 815 applies digital filtering to remove noise from the received lung audio data to obtain filtered lung audio data. Based on user inputs or inputs from the application module control block, lung auscultation audio block 815 may forward the filtered data to one or more of audio play block 820, storage block 880 and transmit block 890. The inputs from the application module control block may be based on whether real-time local play, remote play and local storage are required to be performed. In an embodiment of the present disclosure, lung audio auscultation data are also simultaneously (synchronously) played locally in phone 110 as well as in a remote device (after concurrent or delayed transmission as required by the physician at the remote device), enabling real-time and/or asynchronous diagnosis by the physician at the remote device.

It is noted here that heart sounds have a frequency range of approximately 50-60 Hz. The digital filter(s) used within heart auscultation audio block 810 may use arbitrary magnitude, low pass and high-boost filtering optimized to capture the frequencies of heart audio. High-boost filtering refers to emphasizing (boosting) of high frequency components in the audio without eliminating low frequency components. The digital filter(s) used in lung auscultation audio block 815 are designed to optimize and boost frequencies from approximately 300 Hz to approximately 550 Hz (respiratory frequencies). The filters of blocks 810 and 815 can implemented as fixed FIR (Finite Impulse Response) and IIR (Infinite Impulse Response), or adaptive filters.

Audio play block 820 forwards digital audio data on path 821 to a hardware audio subsystem (which may include digital-to-analog converter (DAC), power amplifier and speaker) in phone 110. Audio play block 820 may be implemented using application programmers interface (API) function call provided by the operating system in phone 110.

Storage block 880 receives data representing audio or video/images from a corresponding block of FIG. 8, formats the data according to corresponding storage formats, and forwards, on path 881, the formatted data to a storage device of phone 110. Storage block 880 may be implemented using application programmers interface (API) function call provided by the operating system in phone 110.

Transmit block 890 receives data representing audio or video/images from a corresponding block of FIG. 8, formats the data according to corresponding transmission formats (including packetizing), and forwards, on path 891, the formatted data to a transmitter of phone 110. Transmit block 890 may be implemented using application programmer interface (API) function call provided by the operating system in phone 110.

Camera interface block 830, otoscopy processing block 835, BP/heart rate/temperature/oximeter block 840, Optical Character Recognition (OCR) block 845 and display block 860 operate on digitized video or image (still picture) data.

Display block 860 forwards, on path 861, to display hardware in phone 110, video/images received from one or more of blocks 845, 835 and 840 on respective paths 856, 836 and 846. The display hardware renders the video/images on a display device (e.g., screen of phone 110). Display block 890 may be implemented using application programmer interface (API) function call provided by the operating system in phone 110.

Camera interface block 830 receives, on path 831, digitized video or image data from camera port 160 and via video hardware (which includes another (ADC)) of phone 110. The video/image may be obtained using otoscope 150, from a finger press of the user's finger on the camera port, or by focusing the camera of phone 110 on display areas of one or more external diagnostic devices such as a digital or analog thermometer, digital or analog blood pressure monitor, digital or analog oximeter, etc.

When otoscope 150 is used, speculum 150A of otoscope 150 is placed (for e.g., by the user) at the body part to be viewed (e.g., ear, nose or throat), and X-Y adjuster 140 is adjusted so that the speculum 150A and lens (in lens holder 150B) are aligned with camera port 160. When a finger press of the user is to be captured, the user adjusts X-Y adjuster 140 to cause speculum 150 and the lens to be moved away from the camera port. When display of an external diagnostic device is desired, the user focuses camera port of camera 110 on the display area of such external diagnostic device.

Camera interface block 830 may be implemented using API function call provided by the operating system in phone 110. Camera interface block 830 forwards, based on inputs from application module control block (noted above), the received video/image data to the corresponding one of blocks 835, 840 and 845, depending on whether the video data is captured using otoscope 150, finger press of user or an external diagnostic device Otoscopy processing block 835 filters the received video/image data obtained using otoscope 150, and forwards the filtered data to one or more of display block 860, storage block 880 and transmit block 890 depending on corresponding inputs received from application module control block (noted above). The inputs from the application module control block may be based on whether real-time local play, remote play and local storage are required to be performed, which in turn may be based on user inputs to the tele-health application. In an embodiment of the present disclosure, the filtered data from otoscopy processing block 835 are simultaneously (synchronously) rendered locally on display block 860 of phone 110 as well as in a display of a remote device (after concurrent transmission to the remote device), enabling real-time diagnosis by the physician at the remote device.

OCR block 845 receives images (captured by the backside camera, for example) of display areas of external diagnostic devices (as noted above), and operates to extract text, numbers, symbol etc., in the images. OCR block 845 forwards the extracted information to one or more of display block 860, storage block 880 and transmit block 890 depending on corresponding inputs received from application module control block (noted above). For example, the external device could be a digital thermometer. The user can obtain his body temperature using the digital thermometer, and OCR block 845 can receive the image of the reading on the display area of the digital thermometer, and extract the temperature value from it.

BP/heart rate/temperature/oximeter block 840 operates to determine the blood pressure (BP), heart rate, body temperature and blood-oxygen saturation level of the user from video/images of a finger press of the user on camera port 160.

The signal processing algorithms in block 480 typically select a region of interest around the approximate center of the field of view (FOV) (in this case, approximately the center of the finger pressed). The size of this FOV region directly affects the computational complexity, and an optimum for the size exists which provides diagnostic quality results, with diminishing returns observed with increasing FOV size. Block 840 extracts the average values for Red/Green/Blue (RGB) channels at a high frame rate, as a function of time. The manner in which each of parameters BP, heart rate, body temperature and blood-oxygen saturation level is determined is now described.

As noted above, block 840 operates on a sequence of RGB images generated by a finger press of the user on camera port 160. Block 840 creates a fixed volume or region of interest (ROI) within each image of the sequence of images. Each image of the sequence is a function of light intensity I, as well as the contents of the ROI on a macroscopic level. Each of the images contains red, green and blue (RGB) values of the sensor (e.g., CMOS) outputs of the camera, and block 840 extracts the average values for Red/Green/Blue (RGB) channels at high frame rate, as a function of time.

The dermal (skin) component of the obtained sequence of images (or more specifically the RGB values of the images) as a function of time is a constant for any given scenario, and the light level variations in the sequence of images is due to the effect of blood flowing in and out of the ROI as the heart goes through the systolic and diastolic phases. Therefore, the light level variations in the sequence of images are also a function of (i.e., correlated with) the user's blood pressure. Thus, the ROI is representative of the heart function and correlates with the blood pressure as a function of time.

The light level values at the peak of a systole are also a function of oxygen content in the blood during the peaks of the systoles. Block 840 corrects for the oxygen content variation by first determining the peaks of the pulses (systolic) corresponding to heart rate based on red intensity values in each image. A systolic peak would correspond to maximum red intensity among all images other than those representing other systolic peaks. Then, block 840 estimates the oxygen content component by subtracting from images representing the systolic peaks, the average value of red intensities in the images corresponding to systolic peaks and extracting oxygen content from flat field-corrected intensities. As is well known in the relevant arts, flat-field correction is a technique used to improve quality in digital imaging by cancelling the effects of image artifacts caused by variations in the pixel-to-pixel sensitivity of the detector (camera) and by distortions in the optical path. The blood oxygen content component thus obtained (or alternatively obtained by averaging estimates of blood oxygen contents over several iterations) indicates the blood-oxygen saturation level.

The heart rate is determined by averaging the period of detected peaks (noted above), and by obtaining an inverse of the period. The body temperature is correlated with heart rate elevation and is an age-dependent factor. Block 840 employs well-known age-heart-rate-temperature relationship to obtain the patient's temperature.

Continuing the description with respect to BP determination, once corrected for blood oxygen content, the only remaining dependent variable is the BP. Block 840 processes multiple successive frames (images) (as an example, the camera may provide 30 frames/second or higher frame rates) to obtain blood volume (correlated with red values in the images) around (i.e., red intensities in image immediately before (with respect to the sequence of images) and immediately after image representing a systolic peak, and red intensities in image immediately before and immediately after image representing a diastolic peak) to determine the rate of volumetric change of blood as a function of time, i.e., dV/dt corresponding to systolic peaks and diastolic peaks.

A region of interest (ROI) is drawn on the approximate center of the finger's image (i.e., in each of the sequence of images). This ROI or the Field of View (FOV) is an arbitrarily small area on the two-dimensional image. The blood flow rate (dV/dt) in and out of this FOV as volumetric change (dV) as function of time (dt) is determined by plotting the corrected (as noted above) red intensities as a function of time by analyzing successive frames thus acquired with its corresponding time stamp (dt).

The rates of volumetric change dV/dt corresponding to systolic peak and diastolic peak are then converted to respective values of dP/dt, i.e., rate of change of pressure with time, through a linear transformation assuming first-degree approximation for a very small part of the pressed finger, further miniaturized by arbitrarily choosing a smaller subset of the image called field-of-view as described earlier. The linear transformation constant K is a function of sensor (camera sensor) response characteristics and can vary from one device to another. This value, i.e., constant K, is determined using a calibration step with known BP.

The BP determined as noted above may contain error components due to the light intensity (lumens) used for obtaining the sequence of images of the finger press and camera resolution variations (across different cameras). Such error components are corrected using commonly known flat-field correction method, in which the sensor (camera elements) response is measured under uniform illumination to establish a baseline. This baseline accounts for any system induced variations, not contributing to the signal of interest and is subtracted from the measured signal as a flat-field correction.

The parameters and signals, such as heart auscultation and lung auscultation audio, images acquired by the otoscope, BP, temperature, blood-oxygen content, etc., as noted in detail above may be termed as diagnostic data.

Thus, various parameters and diagnostic data related to the user's health are obtained and transmitted in real-time to a physician at a remote terminal. The description is continued with a brief illustration of an example user interface provided by application modules (other than those of FIG. 8) on smart phone 110 to enable a user/patient to interact with a physician at the remote terminal, obtain diagnostic measurements, etc.

4. User Interface

Once a tele consultation is setup, the patient and physician connect with each other by opening an application (tele-health application noted above) on their respective smart phones. The patient upon physician's verbal or non-verbal (textual) or sign (video) instructions will click on menu items within the applications (examples noted below) to acquire and synchronously relay the diagnostics information from the point-of-care to a remote physician. Different diagnostic information will be acquired either serially or in parallel based upon the medical needs as seen fit by the health care provider or physician. Upon the completion of diagnostics acquisition, the prescription will be sent to the patient on phone 110, or the pharmacy of their choosing. At the end of the consultation billing related exchanges will happen between the patient and healthcare provider.

FIGS. 9A-9L are example screens provided by the tele-health application that a user interacts with. In each of the screens illustrated, the 'cancel' button at the top-left of the screen cancels the current operation(s), and the user is presented with the next appropriate screen.

FIG. 9A is a screen that is presented on the display of phone 110 to a user upon launching the tele-health application. The user can enter his email ID in box 901 and password in box 902, and then press button 903 to sign-in or register (if not yet registered). Upon signing-in, the user is presented with the screen shown in FIG. 9B.

In FIG. 9B, pressing button 907 allows the user to fix an appointment with a physician, and upon pressing button 907, the user is presented with screen of FIG. 9E. Referring to FIG. 9E, the user can select one of the physicians indicated by reference numerals 920, 921 and 922. Assuming the user selects Lisa Su (920), the user is then presented with the screen of FIG. 9F, in which the user can enter the date (925) and time (926) for the appointment. Pressing the set button 927 generates the screen of FIG. 9G, which displays the physician's name (931), date (932) and time (933) of the appointment. The user can at any time move back to the previous screen by pressing "cancel" (top right of all screens). Alternatively, the facility to select and fix appointments with a physician (as described above) is automatically presented to the user (rather than via pressing of button 907) after clicking on button 905, and completing the triaging questionnaire, as noted next.

In FIG. 9B, pressing button 905 leads the user to screen of FIG. 9C for triaging questions. As indicated in FIG. 9C, a questionnaire is presented with questions regarding specific health conditions (911, 912, 913). The user can select one or more of the health conditions, and press button 914, upon which the user is presented with screen of FIG. 9D. In FIG. 9D, health conditions are presented (915, 916, 917 and 918), which the user can select based on his health condition. Upon completion of the triaging questionnaire, the answers provided are transmitted to the remote terminal where the remote physician will use it for diagnostics. Additionally, the user is presented with options of available healthcare professionals for consultation, as described above with respect to pressing of button 907 and the resulting screens.

In FIG. 9B, button 906 is for initiating a consultation with a physician with whom an appointment has already been fixed as, noted above. Alternatively, the consultation can be initiated upon completion of fixing an appointment with a physician as noted above, and if the physician is currently available for consultation. In either case, the user is then presented with the screen of FIG. 9H. The consultation is enabled by the tele-health application placing an audio and/or video call with the remote physician. Once the call is established, the user is presented with the screen of FIG. 9H.

The screen of FIG. 9H enables the user, under direction of the physician at the remote end, to generate diagnostic data, such as heart/lung auscultation audio data using stethoscope 130, otoscopy data using otoscope 150/600, diagnostic data relating to temperature, blood pressure, blood oxygen content and heart rate from a finger-press on the camera port, and also diagnostic data captured by external devices and obtained by OCR block 845, as described above, thereby facilitating a complete medical examination.

Specifically, pressing of button 941 (with stethoscope's (130) auscultation piece 130A placed on heart area of the user), initiates capture of heart auscultation audio data via stethoscope 130, with the user being presented with screen of FIG. 9I. FIG. 9I indicates that the heart auscultation data is being filtered by 'Filter I', which is executed by heart auscultation audio block 810 (FIG. 8).

Pressing of button 942 (with stethoscope's (130) auscultation piece 130A placed on lung area of the user), initiates capture of lung auscultation audio data via stethoscope 130, with the user being presented with screen of FIG. 9J. FIG. 9J indicates that the lung auscultation data is being filtered by 'Filter II', which is executed by lung auscultation audio block 810 (FIG. 8).

Pressing of button 943 (with otoscope's (150) speculum 150A/610 placed on ear/nose/throat of user, and optionally pressing the flash of the camera when otoscope 600 is used), initiates capture of video data via otoscope 150, with the user being presented with screen of FIG. 9K. FIG. 9K indicates that video data is being filtered by 'Filter III', which is executed by otoscopy processing block 835 (FIG. 8). The screen also displays parameter 1, the temperature of the patient (951) determined by block 840.

Pressing of button 944 (with otoscope's (150) speculum 150A/610 placed on ear/nose/throat of user, and optionally pressing the flash of the camera when otoscope 600 is used), initiates capture of video data via otoscope 150, with the user being presented with screen of FIG. 9L. FIG. 9L indicates that video data is being filtered by 'Filter IV', which is executed by otoscopy processing block 835 (FIG. 8). The screen also displays parameter 2 (Blood Pressure) (961), parameter 3 (pulse oxygen content) (962), and parameter 4 (pulses per minute) (963) determined by block 840.

It is noted here that the tele-health application provided by the present disclosure can generate various other screens also for display of various other options and information to the user, and the screens of FIGS. 9A-9L are merely representative. Further, a counterpart application is provided by the present disclosure and is installed in the remote device to complement the operation of the modules (or tele-health application) in phone 110 and to enable the two-way audio/video consultation described herein. Such application can be implemented in a known way by one skilled in the relevant arts upon reading the disclosure herein.

Several other features of the tele-health application not described above are summarized below, some of which have also been noted in other sections of this disclosure:

(A) Regulatory Compliance
1. HIPAA (Health Insurance Portability and Accountability Act)-compliant patient and provider registration portal with two factor authentication.
2. HIPAA-compliant patient and provider login web portal hosted on cloud or private cloud or private server machines.
3. HIPAA-compliant login to androßid and iOS apps with below functionality:
   1. Login using ID/Email and password/fingerprint/face ID
   2. Online mode
      i. Both Video Calling and diagnostic features will be accessible
      ii. The ability to use additional features while in a two way conference call
   3. Offline mode
      i. Only the diagnostics features are accessible with on-device archiving and delayed relay ability to the remote location (No video calling)

(B) Appointment and User Management Features
1. Two modes for the login
   1. Patient mode
      1. In patient mode when an appointment is made, a link is sent via e-mail and added to the calendar in the phone, by clicking the link the two clients can connect via video call.
   2. Provider mode
      1. Review the appointment calendar
      2. Appointment calendar to have active links which when clicked would start the WebRTC video call (C) Video Call Features
1. Mute microphone
2. Switch off front-side camera thereby permitting only audio-call.
3. Switch between the back and front camera
4. Zoom in and out the cameras.
5. Switch to otoscope mode in which the object under otoscopy is zoomed into and displayed on the local screen as well as remote screen.
6. Switch between three different audio filters for real time/Synchronous transmission of the auscultation audio seamlessly over WebRTC or equivalent technology.

(D) Additional Features
1. If an earphone with a microphone is connected to the phone, then the tele-health application generates an error message saying that the additional features (stethoscope and otoscope) cannot be used.
2. In offline mode audio is not sent to the remote device via WebRTC, but made available on the earphones (in ear-buds type, approved earphones).
3. In offline mode audio can be recorded and saved on the phone or the cloud or emailed only via tele-health-app.
4. The saved audio, other user entered data will have meta-data of the user name, birthdate, time, mode (clean channel, filter 1 or filter 2) and date of the recording.
5. User is allowed to replay the recordings.
6. User is allowed to delete the recordings.
7. User is warned before deleting the recordings (or any other user data) that they can't be retrieved
8. There are app buttons to switch between different filters. The filters are as follows
   1. Clean channel with no filtering
   2. Heart mode auscultation
   3. Lung mode auscultation
9. Finger press of the patient on the back-side camera is followed by a user input (button press) on a corresponding screen (not shown).

Example internal details of phone 110 are described next.

5. Phone

FIG. 10 is a block diagram illustrating the implementation details of mobile/smart phone 110 in an embodiment of the present disclosure. Although noted as a mobile phone, device 110 may in general be implemented as a digital processing device having wireless or wired communication capabilities, such as for example, tablet PC (personal computer), iPads, internet-connected chrome books, computers, IoT (Internet of Things) enabled devices as well as wired telephones, IP (internet protocol) phones, etc., as also note above.

Mobile phone 110 is shown containing battery 1001, power supply 1005, microphone interface 1010, camera interface 1015, processing block 1020, non-volatile memory 1030, random access memory (RAM) 1040, input block 1050, display 1060, transmit chain 1070, receive chain 1080, switch 1090 and antenna 1095. The specific components/blocks of mobile phone 1000 are shown merely by way of illustration. However, mobile phone 1000 may contain more or fewer components/blocks.

Battery 1001 in conjunction with power supply 1005 provides a regulated power supply voltage which powers each of blocks 1010, 1015, 1020, 1030, 1040, 1050, 1060, 1070 and 1080. However, in FIG. 10, only the power connection to processing block 1020 is shown for clarity.

Microphone interface 1010 receives audio signals on path 180 (microphone port), amplifies the signals, and generates digital data representing the signals using ADC. Microphone interface 1010 forwards the digital audio data to processing block 1020 for further processing.

Camera interface 1015 receives light (visible/infra-red, etc.) via camera port 160, and generates digital video and/or still images in a known way. Thus, for example, camera interface 1015 may contain RGB filters, image sensor (e.g., CMOS), ADC, formatting circuits, etc., to generate videos/ images in the form of sets of RGB values. Camera interface 1015 forwards the RGB values to processing block 1020.

Input/output block 1050 represents one or more input devices and output devices used to provide user inputs to mobile phone 1000, and output data from mobile phone 110 to a user. Thus, input/output block 1050 may include a keypad as input and DAC, power amplifiers and speakers/ earphones as output. Display 1060 represents a display screen (e.g., liquid crystal display) to display images/text generated by processing block 1020.

Antenna 1095 operates to receive from, and transmit to, a wireless medium, information-bearing wireless signals. Switch 1090 may be controlled by processing block 1020 (connection not shown) to connect antenna 1095 either to receive chain 1080 via path 1098, or to transmit chain 1070 via path 1079, depending on whether mobile phone 1000 is to receive or transmit wireless signals.

Transmit chain 1070 receives data/speech/audio/video (in general information signal, including those generated by transmit block 890 when executed by processing block 1020) transmitted from processing block 1020, generates a radio frequency (RF) signal modulated by the information signal according to corresponding standards such as GSM, CDMA, etc., and transmits the RF signal via switch 1090 and antenna 1095. Receive chain 1080 receives an RF signal bearing an information signal (including signals representing data from the remote device noted herein) via switch 1090, path 1098 and antenna 1095, demodulates the RF signal, and provides the extracted information (data/speech/ audio/video) to processing block 1020.

Non-volatile memory 1030 is a non-transitory machine readable storage medium storing instructions, which when executed by processing block 1020, causes mobile phone 1000 to provide several features described herein. Thus, non-volatile memory 1030 may store instructions representing the application modules noted herein, including those of FIG. 8. Non-volatile memory 1030 also stores data, such as that on path 881 (FIG. 8). RAM 1030 is a volatile random access memory, and may be used for storing instructions and data.

Processing block 1020 (or processor in general) may contain multiple processing units (processors) internally, with each processing unit potentially being designed for a specific task. Alternatively, processing block 1020 may contain only a single general-purpose processing unit. Processing block 1020 may execute instructions stored in non-volatile memory 1030 or RAM 1040 to enable mobile phone 110 to operate to provide various features described herein. Specifically, processing block 1020 executes instructions contained in the tele-health application, including the application modules of FIG. 8, modules that generate the screens of FIGS. 9A-9L, the application module control block, etc., to provide a two-way audio and/or video consultation between a user and a remote medical professional or physician in real-time. Paths 821, 881, 891, 861, 801 and 831 of FIG. 8 are contained in paths 1052, 1032, 1027, 1062, 1021 and 1025 respectively.

6. Conclusion

References throughout this specification to "one embodiment", "an embodiment", or similar language means that a particular feature, structure, or characteristic described in connection with the embodiment is included in at least one embodiment of the present disclosure. Thus, appearances of the phrases "in one embodiment", "in an embodiment" and similar language throughout this specification may, but do not necessarily, all refer to the same embodiment.

While in the illustrations of FIGS. 1-4, 5A, 5B and 10, although terminals/nodes are shown with direct connections to (i.e., "connected to") various other terminals, it should be appreciated that additional components (as suited for the specific environment) may also be present in the path, and accordingly the connections may be viewed as being "electrically coupled" to the same connected terminals.

While various embodiments of the present disclosure have been described above, it should be understood that they have been presented by way of example only, and not limitation. Thus, the breadth and scope of the present disclosure should not be limited by any of the above-described embodiments, but should be defined only in accordance with the following claims and their equivalents.

What is claimed is:

1. An A tele-health apparatus for use in combination with a telephone having a microphone and a camera, said tele-health apparatus for facilitating remote examination of a living-being, the tele-health apparatus comprising:
   an auscultation piece to acquire sounds made by body of said living-being;
   an otoscope to obtain images of a part of said living-being;
   an adjuster;
   a solid medium coupled at a first end to said auscultation piece; and
   a mechanical structure to grip said telephone and also attached to a second end of said solid medium, said second end being attached proximal to said microphone to cause said acquired sounds to be transmitted from said auscultation piece to said microphone,
   a first end of said adjuster also being physically attached to said mechanical structure, and a second end of said adjuster being attached to said otoscope, said adjuster being adjustable to place said otoscope in front of said camera to enable said camera to receive said images from said otoscope,
   whereby said acquired sounds and said images are transmitted by said telephone to a remote person to facilitate remote examination of said living-being.

2. The apparatus of claim 1, wherein said auscultation piece is part of a stethoscope, and said solid medium is a windpipe of the stethoscope.

3. The apparatus of claim 1, wherein said images comprise still pictures or videos of said part.

4. The apparatus of claim 3, wherein said adjuster is an X-Y adjuster, wherein said otoscope comprises a speculum attached to said X-Y adjuster, said X-Y adjuster being pivoted to said mechanical structure via a pivot mechanism to place said otoscope in front of said camera in one position and away from said camera in a second position.

5. The apparatus of claim 2, wherein said solid medium has a sufficient length so that a user can simultaneously view and hear a physician at a remote device via said telephone, while simultaneously being able to operate said stethoscope.

6. The apparatus of claim 3, wherein said camera is on the back-side of said telephone, said otoscope further comprising light guides to contain optic fibers, wherein said optic fibers are connected to a flash light emitting diode (LED) of said telephone, thereby enabling capture of images from objects illuminated by said flash.

7. The apparatus of claim 3, wherein said otoscope contains a first lens and a first optical filter, said first lens to magnify the object to be viewed, wherein said first optical filter is designed to convert infra-red light to visible light.

8. The tele-health apparatus of claim 1, wherein said second end of said solid medium comprises a coupling piece, said coupling piece being coupled to said mechanical structure through a compression fit mechanism, said coupling piece also comprising one or more suction cups or rubber couplers to allow a user's voice to be captured by said microphone without significant attenuation, whereby said user can conduct audio communication also using said microphone without significant degradation.

\* \* \* \* \*